United States Patent
Olson et al.

(10) Patent No.: US 9,827,056 B2
(45) Date of Patent: Nov. 28, 2017

(54) MEDICAL DEVICE POSITIONER FOR REMOTE CATHETER GUIDANCE SYSTEMS

(71) Applicant: St. Jude Medical, Atrial Fibrillation Division, Inc., St. Paul, MN (US)

(72) Inventors: Eric S Olson, Maplewood, MN (US); Mark B. Kirschenman, Waverly, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 536 days.

(21) Appl. No.: 13/790,622

(22) Filed: Mar. 8, 2013

(65) Prior Publication Data
US 2014/0257327 A1    Sep. 11, 2014

(51) Int. Cl.
A61B 34/30    (2016.01)
A61B 17/00    (2006.01)
A61M 25/01    (2006.01)

(52) U.S. Cl.
CPC .... *A61B 34/30* (2016.02); *A61B 2017/00477* (2013.01); *A61B 2034/301* (2016.02); *A61M 2025/0175* (2013.01)

(58) Field of Classification Search
CPC ............... A61B 19/22; A61B 19/2203; A61B 2019/2211; A61B 2019/2215;
(Continued)

(56) References Cited

U.S. PATENT DOCUMENTS 4,549,538 A * 10/1985 Schadrack, III ... A61B 17/1633
606/104
4,909,798 A    3/1990 Fleischhacker et al.
(Continued)

FOREIGN PATENT DOCUMENTS

EP    0654244    5/1995
WO    02/065933    8/2002
(Continued)

OTHER PUBLICATIONS

International search report and written opinion in PCT application No. PCT/US2014/019899 (dated Jun. 16, 2014).

*Primary Examiner* — Jocelin Tanner
(74) *Attorney, Agent, or Firm* — Dykema Gossett PLLC

(57) ABSTRACT

A medical device positioner for use with a remote catheter guidance system (RCGS) is provided, which can address angular, lateral and/or translational misalignment of an elongate medical device between the RCGS and an access point on a patient's body. Such a medical device positioner can comprise a base configured to attach to a remote catheter guidance system and a first support member extending from the base and having a receiving portion for receiving at least a portion of the elongate medical device. The medical device positioner can further include a second support member movably coupled to the first support member and including a second receiving area sized and configured to receive at least a portion of the elongate medical device. The medical device positioner can also include first and second tube sections with at least a portion of the first tube section being adapted to be inserted into a vascular system of a patient at an access point. A joint septum can be included for connecting the first and second tube sections.

9 Claims, 13 Drawing Sheets

(58) Field of Classification Search
CPC ........ A61B 2019/2219; A61B 18/1492; A61B 1/00147; A61B 1/00149; A61B 17/00234; A61B 34/70; A61B 2034/301; A61B 2034/302; A61B 34/00; A61B 34/30; B25J 9/10; A61F 2002/9665; A61F 2/966

See application file for complete search history.

(56) References Cited

U.S. PATENT DOCUMENTS

| | | | |
|---|---|---|---|
| 5,092,857 | A | 3/1992 | Fleischhacker |
| 5,827,313 | A * | 10/1998 | Ream ............... A61B 5/0066 600/471 |
| 6,233,476 | B1 | 5/2001 | Strommer et al. |
| 6,498,944 | B1 | 12/2002 | Ben-Haim et al. |
| 6,690,963 | B2 | 2/2004 | Ben-Haim et al. |
| 6,788,967 | B2 | 9/2004 | Ben-Haim et al. |
| 7,197,354 | B2 | 3/2007 | Sobe |
| 7,263,397 | B2 | 8/2007 | Hauck et al. |
| 7,386,339 | B2 | 6/2008 | Strommer et al. |
| 8,317,744 | B2 | 11/2012 | Kirschenman et al. |
| 8,317,745 | B2 | 11/2012 | Kirschenman et al. |
| 8,343,096 | B2 | 1/2013 | Kirschenman et al. |
| 2002/0099435 | A1* | 7/2002 | Stinson ............... A61F 2/90 623/1.12 |
| 2002/0177789 | A1* | 11/2002 | Ferry ............... A61B 1/00147 600/585 |
| 2005/0234293 | A1* | 10/2005 | Yamamoto ......... A61B 1/00082 600/102 |
| 2005/0283137 | A1* | 12/2005 | Doyle ............... A61B 17/1222 606/1 |
| 2006/0184226 | A1* | 8/2006 | Austin ............... A61F 2/95 623/1.11 |
| 2007/0137371 | A1* | 6/2007 | Devengenzo ...... A61B 19/2203 74/490.01 |
| 2009/0247943 | A1 | 10/2009 | Kirschenman et al. |
| 2009/0248042 | A1 | 10/2009 | Kirschenman |
| 2010/0191050 | A1 | 7/2010 | Zwolinski |
| 2010/0256558 | A1 | 10/2010 | Olson et al. |
| 2010/0274078 | A1* | 10/2010 | Kim ............... A61B 1/00149 600/102 |
| 2011/0015569 | A1 | 1/2011 | Kirschenman et al. |
| 2011/0015647 | A1* | 1/2011 | Salisbury, Jr. ......... A61B 19/26 606/130 |
| 2011/0130718 | A1* | 6/2011 | Kidd ................ A61M 25/0133 604/95.01 |
| 2012/0197190 | A1* | 8/2012 | Suon .................. A61B 17/2909 604/95.04 |

FOREIGN PATENT DOCUMENTS

| | | |
|---|---|---|
| WO | 02/089872 | 11/2002 |
| WO | 2009120982 | 10/2009 |

* cited by examiner

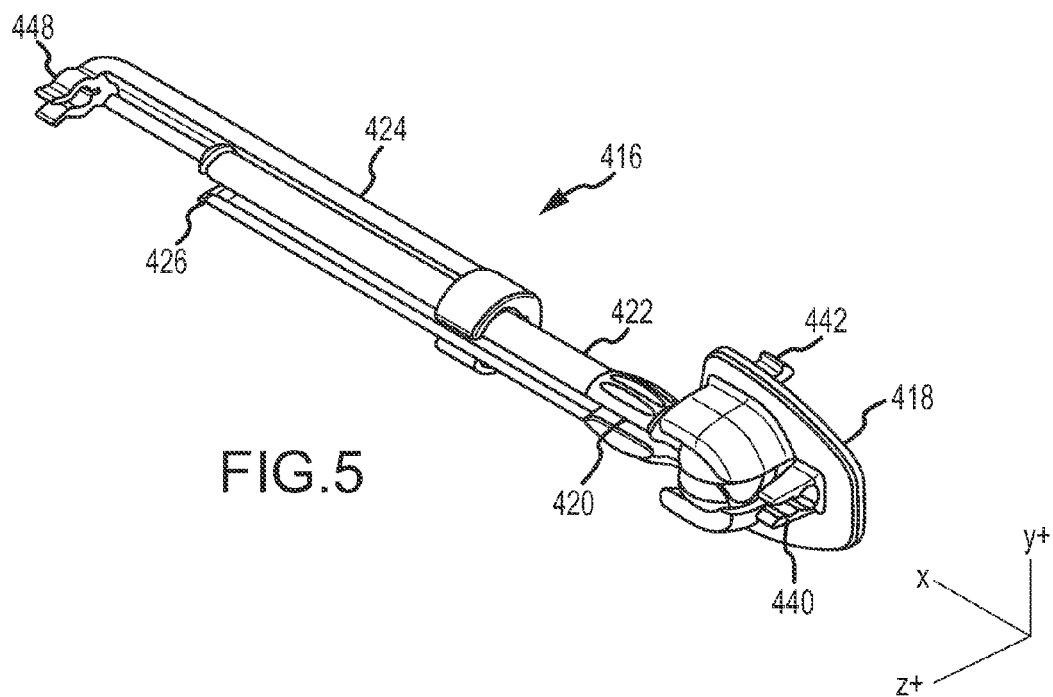

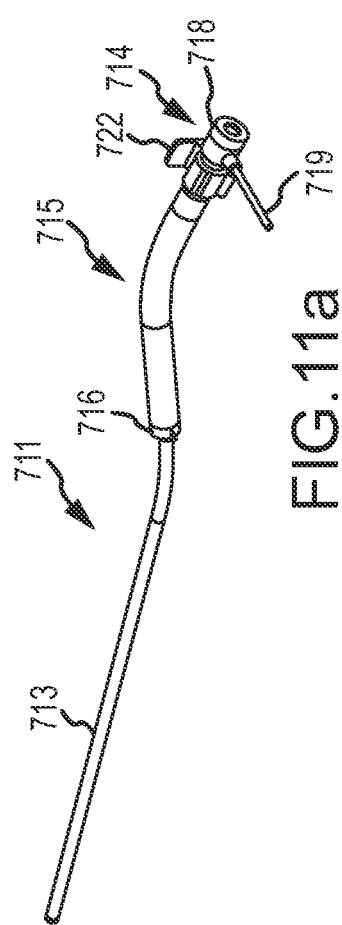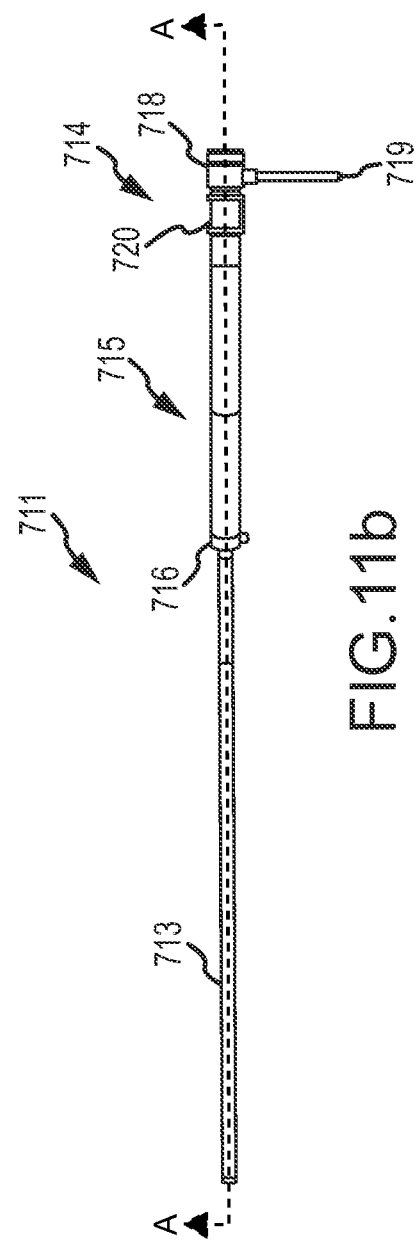

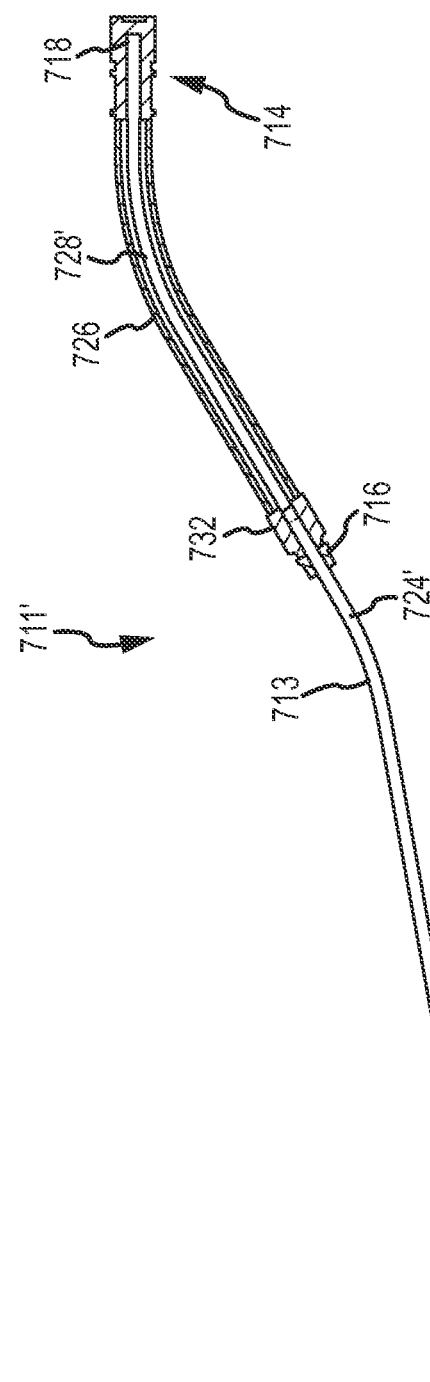

MEDICAL DEVICE POSITIONER FOR REMOTE CATHETER GUIDANCE SYSTEMS

BACKGROUND a. Field

The instant disclosure relates generally to guiding elements for elongate medical devices used with remote catheter guidance systems (RCGSs), and specifically to a positioner for guiding a catheter during automated use of an RCGS.

b. Background Art

Electrophysiology (EP) catheters are used in a variety of medical procedures, including, for example, diagnostic, therapeutic, mapping and ablative procedures. Catheters are used to correct conditions such as atrial arrhythmia, including for example, ectopic atrial tachycardia, atrial fibrillation, and atrial flutter. Typically, a catheter is manipulated through the patient's vasculature to an intended site, for example, a site within the patient's heart, and carries one or more electrodes, which may be used for mapping, ablation, diagnosis, or other treatments.

Advancing a catheter into a patient and to the intended site generally requires a physician such as an electrophysiologist to physically handle the catheter and move it into the patient. In a conventional approach, an introducer is first inserted through the skin surface at an access site on a patient's body and sutured to the body to prevent motion relative to the patient. The electrophysiologist then inserts a sheath for a catheter, or a catheter alone, into the introducer opening at the access site and threads it through the vasculature to a region of interest. The sheath and/or catheter must be manually guided into the introducer at the access site, which can include a hemostasis valve, at the access point.

Recently, remote catheter guidance systems (RCGS) (or robotically controlled medical device guidance systems) for one or more medical devices have been used to facilitate precision control of a medical device during a procedure. In general, these types of systems carry out (as a mechanical surrogate) input commands of a clinician or other end-user to deploy, navigate, and manipulate one or more medical devices, such as, for example, a catheter and/or an introducer or sheath for a catheter, or some other elongate medical instrument. One exemplary remote catheter system is described and depicted in U.S. patent application Ser. No. 12/347,811 (published as United States patent application publication no. US 2009/0247993 A1) the entire disclosure of which is incorporated herein by reference.

A conventional RCGS typically includes, among other components, a manipulator assembly and one or more medical device cartridges. Each medical device cartridge has a medical device (e.g., a catheter or sheath) coupled therewith, and is configured to be mounted on, or attached to, a corresponding manipulation base of the manipulator assembly. When a medical device cartridge is attached to the manipulation base, the manipulator assembly is configured to maneuver the medical device associated with the medical device cartridge by, for example, translating the device cartridge back and forth in a linear fashion.

In addition to the increased precision control, another benefit of an RCGS is that an electrophysiologist or other end-user can operate the manipulation of a catheter through an input control system while having access to a visualization system that displays, for example, the location of the catheter. Such control system and visualization system can be located at the patient site or at a remote location.

The foregoing discussion is intended only to illustrate the present field and should not be taken as a disavowal of claim scope.

BRIEF SUMMARY

In various embodiments, a medical device positioner can be provided for a remote catheter guidance system, the positioner being configured to eliminate or minimize buckling of an elongate medical device during automatic manipulation by the remote catheter guidance system. One embodiment of such a medical device positioner can include a base configured to attach to a remote catheter guidance system and a first support member extending from the base. The first support member can define a receiving portion that is sized and configured to receive at least a portion of an elongate medical device. The medical device positioner can include a second support member that is movably coupled to the first support member and also defines a second receiving area sized and configured to receive at least a portion of the elongate medical device. The medical device positioner can further include a hemostasis valve positioned at the base.

In another embodiment, a medical device positioner can include a base configured to attach to a remote catheter guidance system and a substantially rigid first support member extending from and pivotably attached to the base. The first support member can define a receiving portion that is sized and configured to receive at least a portion of an elongate medical device. The medical device positioner can be attached to the base by means of a ball and socket joint. A locking member radially disposed around the first support member can also be included and the locking member can be configured to secure at least a portion of an elongate medical device in the receiving portion of the first support member.

Another embodiment of a medical device positioner can include a base configured to attach to a remote catheter guidance system and a first support member extending from the base. The first support member can include first and second tube sections, at least a portion of the first tube section being adapted to be inserted into a vascular system of a patient at an access point. The second tube section can be located proximal to the first tube section and there can be a joint septum connecting the first tube section and the second tube section. The first and second tube sections can be connected such that the proximal end of the second tube section is inserted into the distal end of the first tube section. Alternatively, the distal end of the first tube section can be inserted into the proximal end of the second tube section. The medical device positioner can also include an annular suture ring attached to and around the first tube section and adapted to be secured to a patient's body at an access point. A flexible jacket tube can further be radially disposed around at least a portion of the second tube section and can be constructed of, for example, interlocking ball and socket segmented tubing, spiral wound metal tubing or skive cut solid tubing. The medical device positioner can further include an irrigation port located at the proximal end of the second tube section.

Further embodiments to address the issues noted above are also possible. For example, one embodiment includes a positioner assembly for positioning an elongate medical device during use with a remote catheter guidance system. The positioner assembly comprises a positioner mount configured for attachment to the remote catheter guidance system and a substantially rigid tube pivotably attached to the positioner mount at the proximal end of the rigid tube. The substantially rigid tube can be configured to align the elongate medical device between the positioner mount and an access point on a patient's body before and during use of the remote catheter guidance system.

Another embodiment includes an introducer for a catheter for use with a remote catheter guidance system. The introducer can comprise first and second hollow tubes axially connected to each other at a joint septum. A portion of the first hollow tube can be adapted to be inserted into a vascular system of a patient at an access point. An annular suture ring adapted to be secured to a patient's body at an access point can be disposed around and attached to the first hollow tube. The proximal end of the second hollow tube can include a hemostasis valve for receiving a catheter and means for attachment of the introducer to the remote catheter guidance system. Further, a flexible jacket tube radially disposed around at least a portion of the second hollow tube can be included. The first and second hollow tubes provide a guide for the catheter to be inserted into the vascular system of a patient, while the flexible jacket tube is configured to align the catheter between the remote catheter guidance system and an access point on a patient's body before and during use of the remote catheter guidance system.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 5 is an isometric view of the medical device positioner of FIG. 4, shown in an open and partially-extended position.

FIG. 7c is a view of the underside of the medical device positioner illustrated in FIG. 7a.

FIG. 11a is an isometric view of the medical device positioner of FIG. 10.

FIG. 11b is a top view of the medical device positioner of FIG. 11a.

FIG. 13b is a top view of the medical device positioner of FIG. 13a.

FIG. 14 is a cross-sectional view along cut line B-B of the medical device positioner of FIG. 13b.

DETAILED DESCRIPTION

Various embodiments are described herein to various apparatuses. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a remote catheter guidance system manipulating one end of medical device used to treat a patient. The term "proximal" refers to the portion of the instrument closest to the remote catheter guidance system and the term "distal" refers to the portion located furthest from the remote catheter guidance system. It will be further appreciated that for conciseness and clarity, spatial terms such as "vertical," "horizontal," "up," "down," "top" and "bottom" may be used herein with respect to the illustrated embodiments. However, surgical instruments may be used in many orientations and positions, and these terms are not intended to be limiting and absolute.

Figure 1:
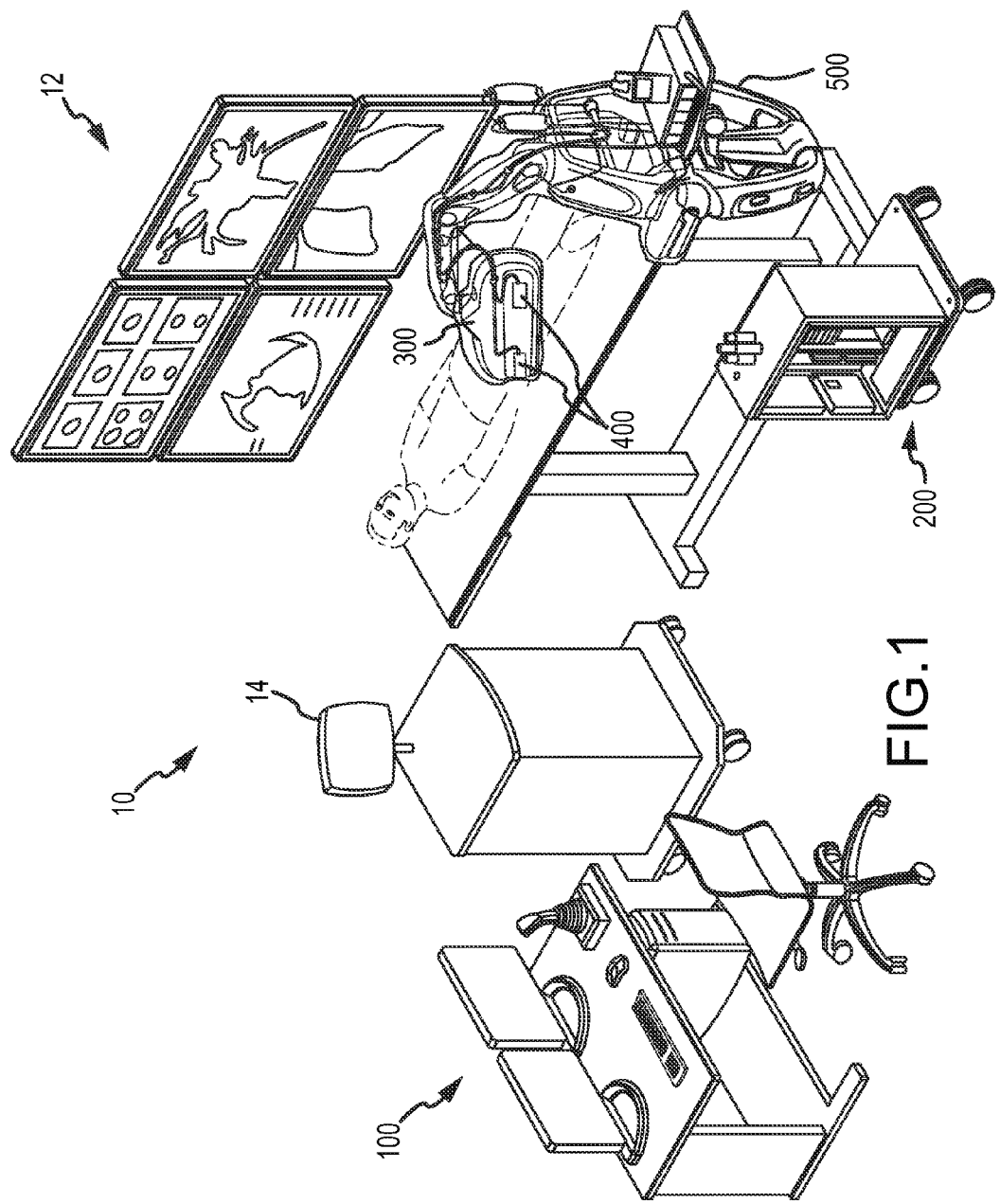
FIG. 1 is an isometric diagrammatic view of a remote catheter guidance system, illustrating an exemplary layout of various system components.

Referring now to the drawings wherein like reference numerals are used to identify the same or substantially similar components in the various views, FIG. 1 illustrates one exemplary embodiment of a remote catheter guidance system 10 (RCGS 10) for manipulating one or more medical devices. The RCGS 10 can be used, for example, to manipulate the location and orientation of catheters and sheaths in a heart chamber or in another body cavity or lumen. The RCGS 10 thus provides the user with a similar type of control provided by a conventional manually-operated system, but allows for repeatable, precise, and dynamic movements. For example, a user such as a physician or electrophysiologist can identify locations (potentially forming a path) on a rendered computer model of the cardiac anatomy. The system can be configured to relate those digitally selected points to positions within a patient's actual/physical anatomy, and can thereafter command and control the movement of the sheath and/or catheter to the defined positions. Once at a specified target position, either the user or the system can perform the desired diagnostic or therapeutic function. The RCGS 10 can enable full robotic navigation/ guidance and control.

As shown in FIG. 1, the RCGS 10 can generally include one or more monitors or displays 12, a visualization, mapping, and/or navigation system 14, a human input device and control system (referred to as "input control system") 100, an electronic control system 200, a manipulator assembly 300 for operating one or more device cartridges 400, and a manipulator support structure 500 for positioning the manipulator assembly 300 in proximity to a patient or a patient's bed.

The visualization, navigation, and/or mapping system 14 may be configured to provide a number of advanced features, such as visualization, mapping, navigation support and positioning (i.e., determine a position and orientation (P&O) of a sensor-equipped medical device, for example, a P&O of a distal tip portion of a catheter). In an exemplary embodiment, the system 14 may comprise an impedance-based system, such as, for example, the EnSite™ NavX™ system commercially available from St. Jude Medical, Inc., and as generally disclosed in U.S. Pat. No. 7,263,397" the entire disclosure of which is incorporated herein by reference. In other exemplary embodiments, however, the system 14 may comprise other types of systems, such as, for example and without limitation: a magnetic-field based system such as the Carto™ System available from Biosense Webster, Inc., and as generally shown with reference to one or more of U.S. Pat. Nos. 6,498,944, 6,788,967, and 6,690,963, the entire disclosures of which are incorporated herein by reference, or the MediGuide™ Technology system available from St. Jude Medical, Inc., and as generally shown with reference to one or more of U.S. Pat. Nos. 6,233,476, 7,197,354, and 7,386,339, the entire disclosures of which are incorporated herein by reference; and a combination impedance-based and magnetic field-based system such as the Carto 3 System also available from Biosense Webster, Inc.

The input control system 100 may be configured to allow a user, such as an electrophysiologist, to interact with the RCGS 10, in order to control the movement and advancement/withdrawal of one or more medical devices, such as, for example, a catheter and/or a fixed sheath and/or a deflectable sheath (see, e.g., U.S. Patent Publication No. 2010/0256558, and PCT/US2009/038597, published as WO 2009/120982, the entire disclosures of which are incorporated herein by reference). Generally, several types of input devices and related controls can be employed, including, without limitation, instrumented traditional catheter/sheath handle controls, oversized catheter/sheath models, instrumented user-wearable gloves, touch screen display monitors, 2-D input devices, 3-D input devices, spatially detected styluses, and traditional joysticks. For a further description of exemplary input apparatus and related controls, see, for example, U.S. Patent Publication Nos. 2011/0015569 and 2009/0248042, the entire disclosures of which are incorporated herein by reference. The input devices can be configured to directly control the movement of the catheter and sheath, or can be configured, for example, to manipulate a target or cursor on an associated display.

The electronic control system 200 can be configured to translate (i.e., interpret) inputs (e.g., motions) of the user at an input device of the input control system 100 (or from another source) into a resulting movement of one or more medical devices (e.g., a catheter and/or a sheath). In this regard, the system 200 may include a programmed electronic control unit (ECU) in communication with a memory or other computer readable media (memory) suitable for information storage. It should be understood that although the visualization, navigation, and/or mapping system 14 and the electronic control system 200 are shown separately in FIG. 1, integration of one or more computing functions can result in a system including an ECU on which can be run both (i) various control and diagnostic logic pertaining to the RCGS 10 and (ii) the visualization, navigation, and/or mapping functionality of system 14.

The manipulator assembly 300, in response to commands issued by the electronic control system 200, can be configured to maneuver the medical device(s) associated therewith (e.g., translation movement, such as advancement and withdrawal of the medical device(s)), as well as to effectuate distal end (tip) deflection and/or rotation or virtual rotation. In an embodiment, the manipulator assembly 300 can include actuation mechanisms/units (e.g., a plurality of electric motor and lead screw combinations, or other electric motor configurations) for linearly actuating one or more control members (e.g., steering wires) associated with the medical device(s) for achieving the above-described translation, deflection and/or rotation (or virtual rotation). Further details of a manipulator assembly can be found in U.S. Patent Publication No. 2009/0247942, the entire disclosure of which is incorporated herein by reference.

A device cartridge 400 can be provided for each medical device controlled by the RCGS 10. For this exemplary description of an RCGS, and as will be described in greater detail below, one cartridge may be associated with a catheter and a second cartridge may be associated with an outer sheath. However, in other exemplary embodiments, a single medical device, and therefore, a single cartridge, or more than two medical devices, and therefore, more than two cartridges, may be used. Accordingly, embodiments wherein more or less than two cartridges are employed remain within the spirit and scope of the present disclosure. Furthermore, medical device form factors other than cartridges 400 may be used with the manipulation assembly 300. In any event, the cartridges (or other medical device form factor) may be coupled, generally speaking, to the RCGS 10 to allow for robotically-controlled movement. Further details of a device cartridge can be found in U.S. Patent Publication Nos. 2009/0247943 and 2009/0247944, the entire disclosures of which are incorporated herein by reference.

Figure 2:
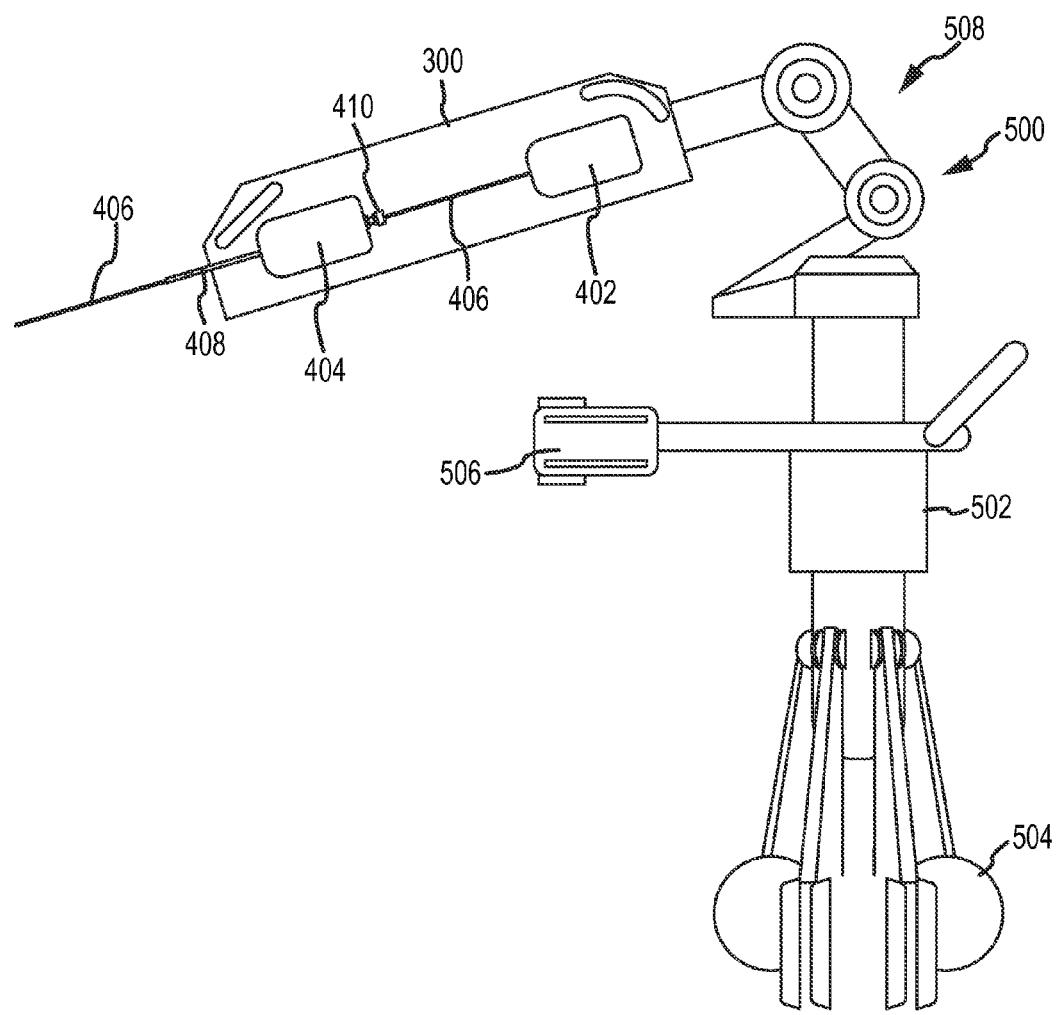
FIG. 2 is a side view of an exemplary manipulator assembly of the system illustrated in FIG. 1 coupled to a robotic support structure.

FIG. 2 is a side view of an exemplary manipulator support structure 500 (see U.S. Patent Publication No. 2009/0247944, the entire disclosure of which was incorporated by reference above) for supporting the manipulator assembly 300. The structure 500 can generally include a support frame 502 including retractable wheels 504 and attachment assembly 506 for attachment to an operating bed (not shown). A plurality of support linkages 508 can be provided for accurately positioning one or more manipulator assemblies, such as the manipulator assembly 300.

Figure 3:
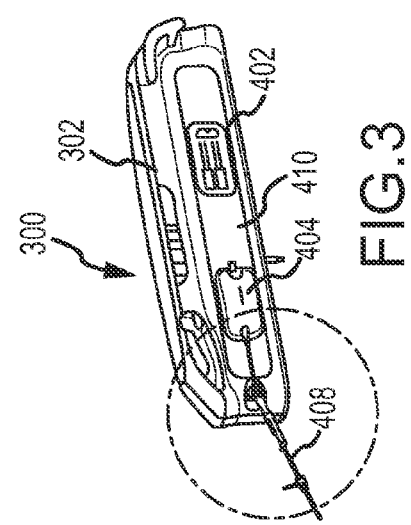
FIG. 3 is an isometric view of another exemplary manipulator assembly of the system illustrated in FIG. 1, including one embodiment of a medical device positioner attached thereto.
Figure 6B:
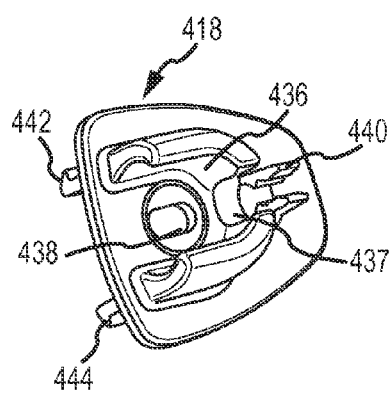
FIGS. 6a-6d are isometric views of the components of the embodiment of a medical device positioner illustrated in FIG. 5.
Figure 6D:
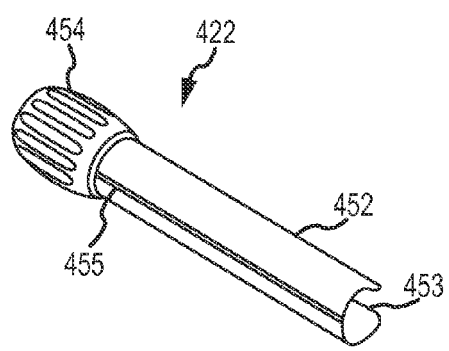
Figure 6A:
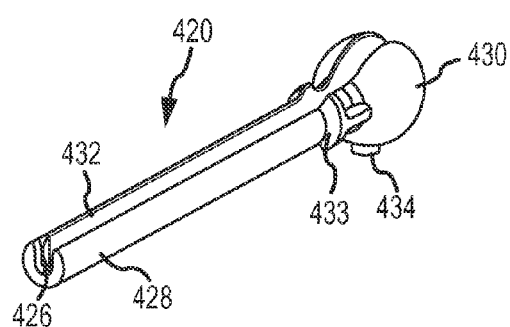
Figure 6C:
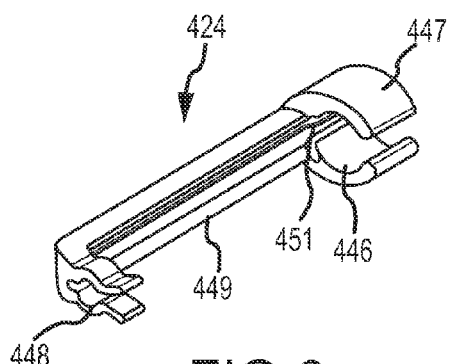

FIG. 3 is an illustration of one embodiment of the manipulator assembly 300. With reference to FIGS. 2 and 3, the manipulator assembly 300 includes a housing 302 and is configured to serve, for example, as the interface for the mechanical control of the movements or actions of one or more device cartridges, such as catheter and sheath cartridges 402, 404. Each device cartridge is configured to receive and retain a respective proximal end of an associated medical device, for example catheter 406 and sheath 408. The assembly 300 also includes one or more plurality of manipulation bases (not shown) onto which the device cartridges are mounted or attached. After mounting, the manipulator assembly 300, through the manipulation bases, is capable of manipulating the attached catheter and/or sheath.

In the illustrated embodiment of FIGS. 2 and 3, the catheter and sheath cartridges 402, 404 are aligned with each other such that catheter 406 can pass through sheath 408 in a coaxial arrangement. Thus, sheath 408 can include a water-tight proximal sheath opening 410 sized to receive the catheter 406 and to let the catheter 406 pass therethrough. Overall, the manipulator assembly 300 is configured to allow not only coordinated movement but also relative movement between catheter and sheath cartridges 402, 404 (and thus relative movement between catheter and sheath). The manipulator assembly 300 of FIG. 3 is shown having only the sheath 408 attached to cartridge 404, but it should be understood that a catheter 406 may be attached to cartridge 402, and inserted into sheath 408 as shown in FIG. 2.

Figure 4:
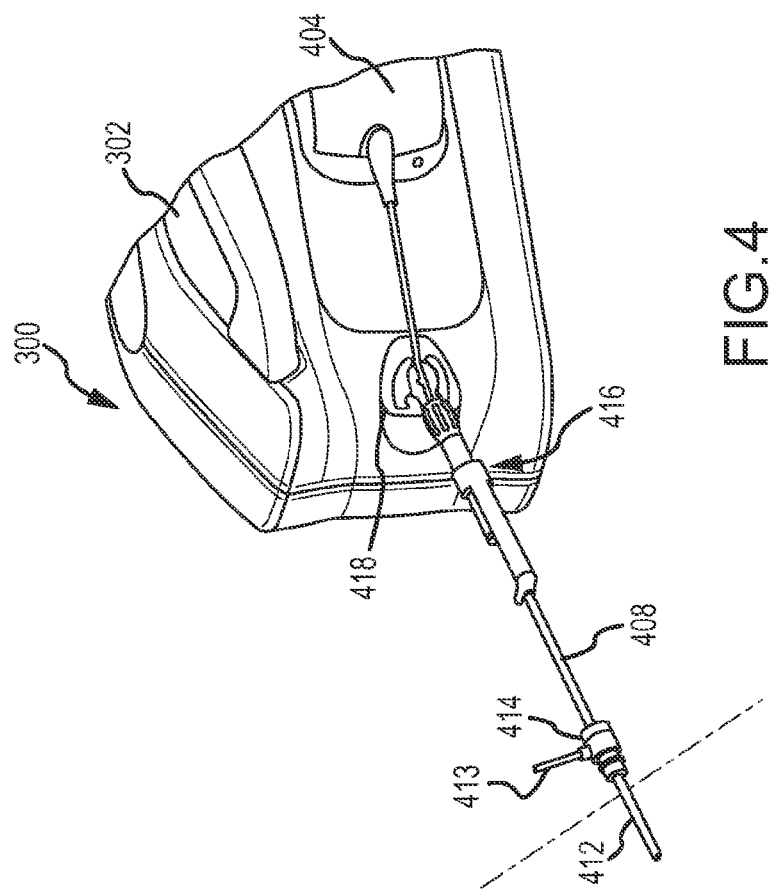
FIG. 4 is an expanded view of one end of the exemplary manipulator assembly of FIG. 3 and the attached medical device positioner.

FIG. 4 illustrates the distal end of the manipulator assembly 300, shown with sheath cartridge 404 and sheath 408, simulating the insertion of sheath 408 into a patient's body. In a typical use of an RCGS 10 for manipulation of a sheath 408 and catheter 406, a conventional introducer 412 is first inserted into the vasculature system of a patient. The sheath 408 (with catheter 406 inserted in sheath 408), is then inserted into the introducer opening 414 and manually advanced to the desired general location in the patient. The introducer 412 can further include an irrigation port 413. The sheath 408 can then be manipulated by the RCGS 10 through the manipulator assembly 300.

Angular, lateral or translational misalignment of the sheath 408 and the introducer opening 406 can result in increased friction between the sheath 408 and the introducer opening 414 during manipulation by the RCGS 10. The increased friction can cause the sheath 408 to buckle or bind, potentially leading to the failure of the sheath 408 or tearing of tissue at the site of the introducer opening 414. Prior RCGS systems are susceptible to such misalignment problems due to the fixed nature of both the sheath cartridge 404, which holds the proximal end of the sheath 408, and the patient, as well as the distance between any support for the sheath 408 and the introducer opening 414. The risk that the sheath 408 may buckle can necessitate the presence of a physician or other user during the procedure to manually guide the sheath 408 if buckling does occur.

An embodiment of a medical device positioner to reduce or eliminate the described problems is shown in FIG. 4. Positioner 416 provides support and direction to the sheath 408 (with or without catheter 406 within it) between the cartridge 404 and the introducer opening 414. The positioner 416 is pivotally mounted to the manipulator assembly 300, allowing the sheath 408 to be better aligned with the introducer opening 414. The positioner further provides support for the sheath 408 at a distance substantially closer to the introducer opening 414. These and other features help reduce the amount of friction between the sheath 408 and introducer opening 414, thus decreasing the risk of buckling to the sheath 408.

Shown in greater detail in FIGS. 5 and 6a-6d, positioner 416 consists of a positioner mount 418 for attachment to the manipulator assembly 300, a barrel 420, a locking tube 422, a support 424 and a barrel tip 426.

Barrel 420 consists of a tube portion 428 and a ball end 430. A slot 432 is located along the entire length of the barrel 420, through tube portion 428 and ball end 430. The slot 432 is sized to accommodate a sheath 408 and/or catheter 406. Shoulder 433 is located between the tube portion 428 and ball end 430. An orientation pin 434 can be located on the ball end 430, opposite the slot 432. Attached at the end of the tube portion 428 opposite the ball end 430 is barrel tip 426, which provides a tapered opening for the slot 432 at the end of tube portion 428.

Positioner mount 418 includes socket 436, configured to engage ball end 430 of barrel 420, creating a ball joint. As is evident from the illustration in FIG. 5, the ball joint allows barrel 420 to pivot about the socket 436 in both the y-axis and z-axis directions, while also allowing it to rotate about the x-axis. The size and shape of the socket 436 can be configured to restrict the range of motion of the barrel 420 in the y-axis direction. In the embodiment shown, positioner mount 418 further includes orientation slot 438 which engages orientation pin 434 on ball end 430 of barrel 420. When pin 434 is engaged in orientation slot 438, the range of motion of barrel 420 in the z-axis direction is limited and the ability of barrel 420 to rotate about the x-axis is substantially restricted. The allowable range of motion of barrel 420 in both the y-axis and the z-axis, and thus the configuration of socket 436 and orientation slot 438, may depend on the desired or allowable bending radius of sheath 408 and/or catheter 406.

Positioner mount 418 further includes guide 440 configured to engage and contain sheath 408. Socket 436 also includes guide slot 437 which allows sheath 408 to pass from guide 440 to the slot 432 in barrel 420. The positioner mount 418 is attached to manipulator assembly 300 through mounting clips 442, 444, located on the positioner mount 418 opposite socket 436. The mounting clips 442, 444 engage mounting slots (not shown) in housing 302 of manipulator assembly 300.

Continuing to refer to FIGS. 5 and 6a-6d, in an embodiment, locking tube 422 is a hollow tube configured to be rotatably fitted around the tube portion 428 of barrel 420. Locking tube 422 consists of a shaft 452 and a grip portion 454 that is designed to facilitate a user manually rotating the tube lock 422 about the tube portion 428. Locking tube 422 is secured on barrel 420 by the shoulder 433 at one end and by barrel tip 426 at the other end of the tube portion 428. A slot 453 is located on one side of locking tube 422 along its entire axial length. The slot 453 is substantially the same size as barrel slot 432 and is configured to facilitate placement of the sheath 408 into the barrel 420 when slot 453 is aligned with barrel slot 432.

Support 424 is an elongate member designed to provide additional support to the sheath 408 at a distance distally beyond the distal end of barrel 420. Support 424 consists at one end of tube tabs 446, 447 sized to substantially surround locking tube shaft 452 and capable of sliding or telescoping along locking tube shaft 452 in an axial direction. At the other end of support 424 is support guide 448 sized to hold sheath 408 while allowing it to slide in an axial direction. Between tube tabs 446, 447 and support guide 448 is support shaft 449 having a concave inside surface which engages the outer surface of the locking tube shaft 452. Support 424 may allow rotational movement of the locking tube 422 relative to the support 424. In another embodiment, support 424 is configured with a lock tab 451 along the length of its internal surface that engages a lock slot 455 located along the length of the outer surface of the locking tube 422 opposite slot 453. When lock tab 451 is engaged with lock slot 455 movement of the support 424 relative to the locking tube 422 is inhibited.

FIG. 5 illustrates the positioner 416 in an open position, allowing for the placement of the sheath 408 into the positioner 416. In FIGS. 4 and 7a-7c the positioner 416 is shown in a closed position (sheath 408 is not shown in FIGS. 7a-7c). In operation, the positioner 416 is placed in the open position, with the locking tube slot 451 aligned with the barrel slot 432. Ball end 430 of barrel 420 is fitted into the socket 436 of positioner mount 418. The sheath 408, with or without the catheter 406 inserted, is then placed into the barrel slot 432 and snapped into support guide 448 and mount guide 440. The locking tube 422 can then be rotated about barrel 420 ensuring that barrel slot 432 is covered by locking tube shaft 452. FIG. 7c shows the underside of positioner 416 of FIG. 7a, with support 424 not shown. The underside view shows the locking tube slot 453 rotated 180° from barrel slot 432 when in the locked position. In other embodiments, the locking tube 422 may be rotated less than 180° about the barrel tube portion 428.

Figure 7A:
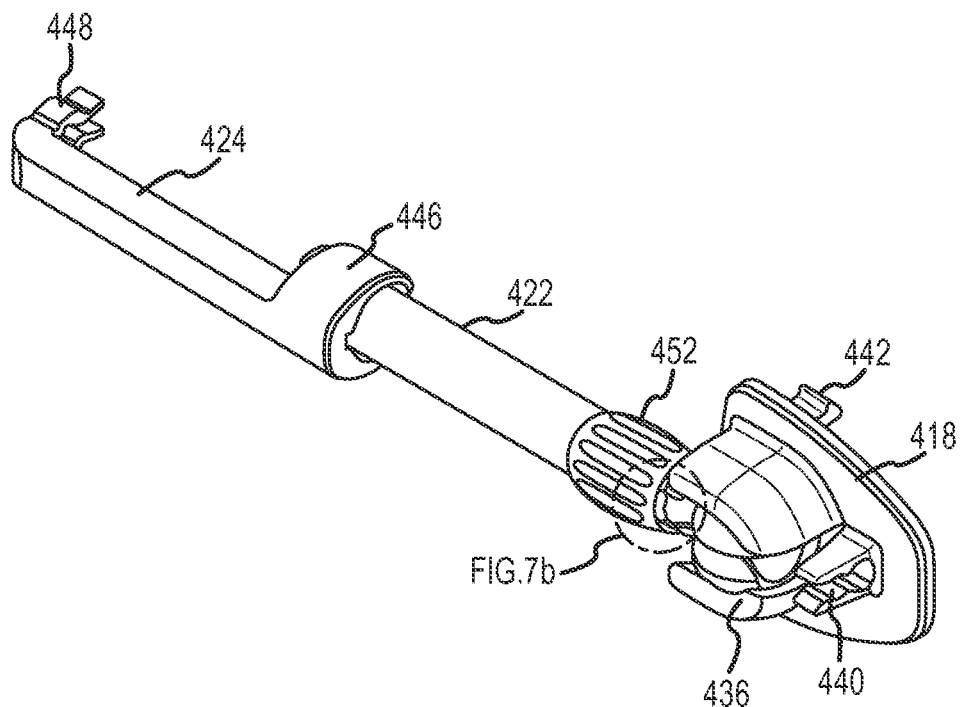
FIG. 7a is an isometric view of the medical device positioner illustrated in FIG. 5, shown in a closed and fully-extended position.
Figure 7B:
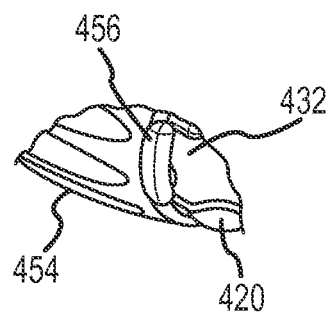
FIG. 7b is an expanded view of a portion of the medical device positioner illustrated in FIG. 7a, showing a locking mechanism.
Figure 7C:
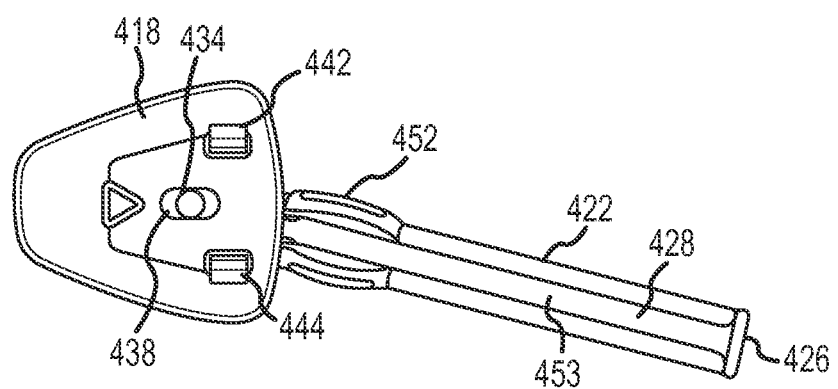

In the embodiment of FIG. 7b, locking tube 422 is secured in a locked position by a locking detent 456, which engages the barrel slot 432. Other mechanisms can be used to secure movement of locking tube 422 relative to barrel 420. Once the sheath 408 is secured in the positioner 416, the positioner mount 418 can be locked into place on the manipulator assembly 300 with mounting clips 442, 444. Alternatively, the positioner mount 418 can be attached to the manipulator assembly 300 before ball end 430 is fitted into socket 436 and/or before the sheath 408 is inserted into barrel slot 432. Additionally, the sheath 408 may be inserted into the introducer opening 414 before or after being fitted into the positioner 416.

During operation of the positioner 416 as described in the preceding embodiments, it is evident that the positioner 416 is in contact with the sheath 408 or other medical device being guided into a patient. Thus, the positioner 416 must be sterile prior to use in a procedure. In an embodiment, the components of the positioner 416 may be constructed of a disposable, lightweight sterilized plastic using injection molding techniques. In another embodiment, the components of the positioner 416 may be constructed of reusable materials (such as stainless steel) which can be re-sterilized for repeated use.

Figure 8:
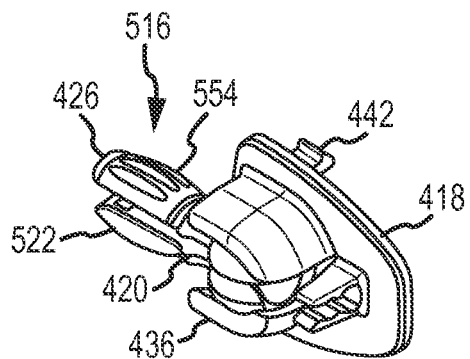
FIG. 8 is an isometric view of another embodiment of a medical device positioner, shown in an open position.

FIG. 8 is another embodiment of a positioner 516, in which the positioner mount 418 is the same as in positioner 416. In the illustrated embodiment, locking tube 522 is comprised entirely of grip portion 554. All other aspects of positioner 16 are substantially similar to positioner 416.

Figure 9:
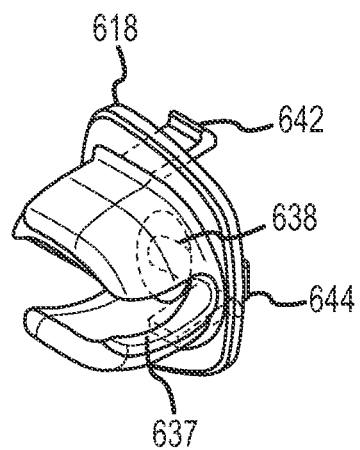
FIG. 9 is an isometric view of another embodiment of a positioner mount for a medical device positioner.

FIG. 9 illustrates another embodiment of a positioner mount 618 for use in the positioner 416 with all other components being the same. Alternative positioner mount 618 is similar to positioner mount 418 as it includes socket 636 for engaging ball end 430 of barrel 420 and guide slot 637 allowing sheath 408 to access slot 432 in barrel 420. Positioner mount 618 further includes mounting clips 642, 644 for attaching to housing 302 of manipulator assembly 300.

In the above described embodiments, misalignment of an elongate medical device between a manipulator assembly of an RCGS and an access point on a patient's body is addressed by a positioner configured to pivot about a point on a distal end of the manipulator assembly and to provide support at a distance between the manipulator assembly and the access point. The described positioner guides an elongate medical device from the manipulation assembly to a patient, in spite of angular, lateral, or distance misalignment. The positioner further allows a procedure to be set up and removed without hindrance.

Figure 10:
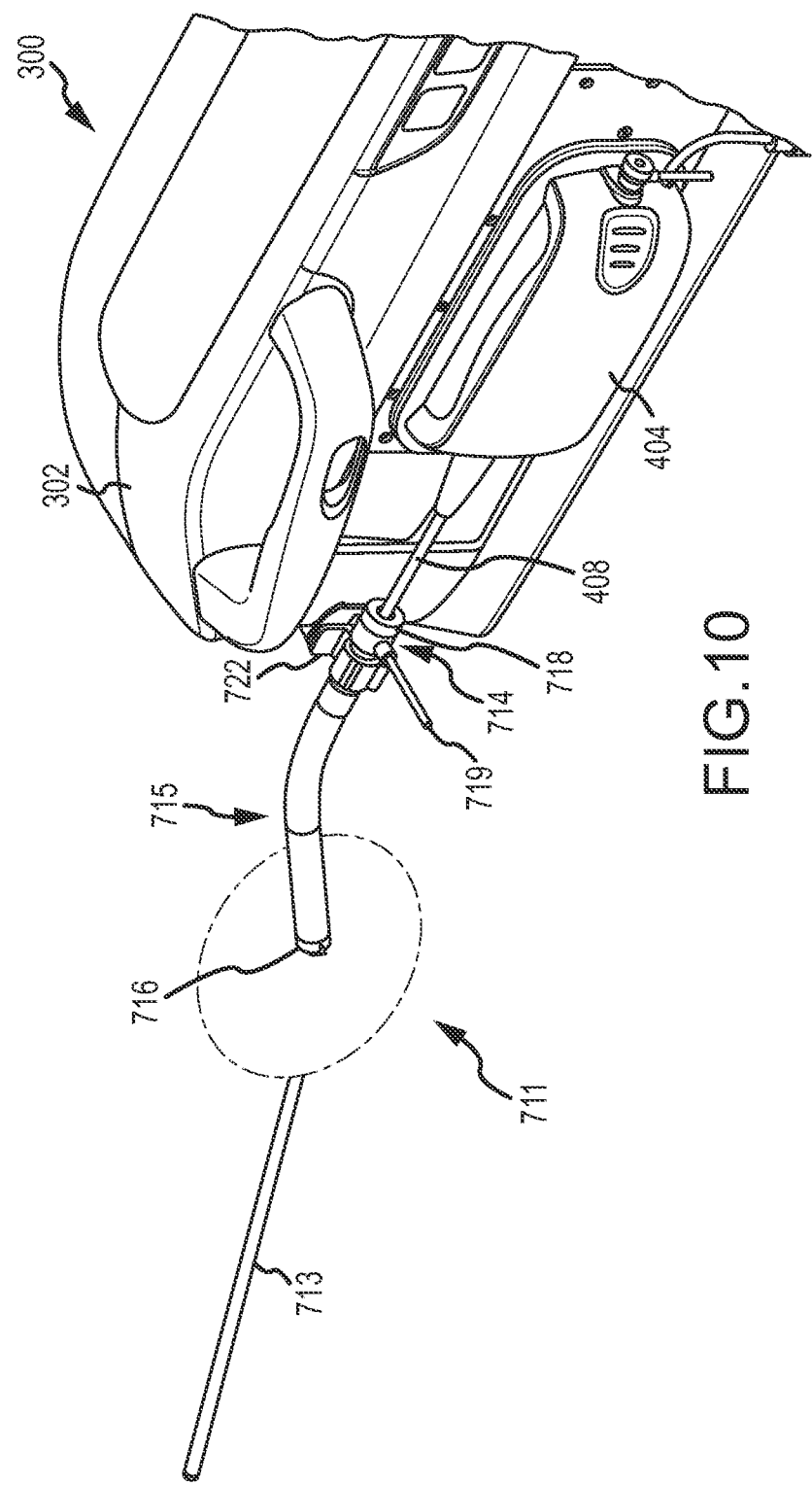
FIG. 10 is an isometric view of the exemplary manipulator assembly illustrated in FIG. 2, with another embodiment of a medical device positioner attached thereto.
Figure 12:
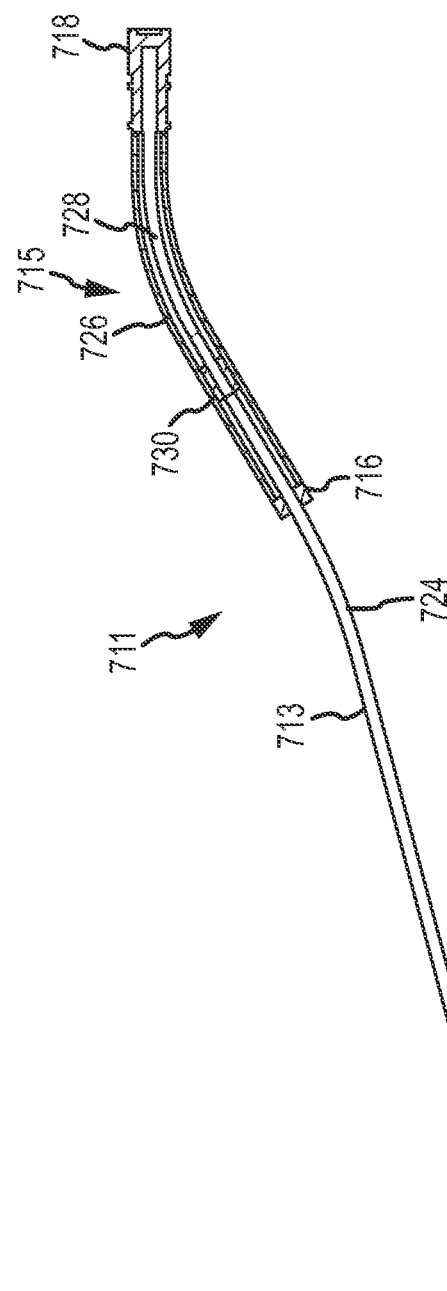
FIG. 12 is a cross-sectional view along cut line A-A of the medical device positioner of FIG. 11b.

An alternative embodiment of a device to address the identified misalignment problems is illustrated in FIGS. 10-12. FIG. 10 shows a catheter guide 711 attached to housing 302 of manipulation assembly 300. FIG. 11a is an isometric view of the catheter guide 711 while FIG. 11b shows a top view of the catheter guide 711. In this embodiment, catheter guide 711 comprises an elongate introducer, or vascular guide section 713 at its distal end, a proximal section 714, a transition section 715 between the vascular guide section 713 and proximal section 714, and an inner lumen 712 extending through the length of the catheter guide 711. An annular stop ring 716 is located between the vascular guide section 713 and the transition section 715. During a procedure, the vascular guide section 713 is inserted into the vasculature of a patient. The annular stop ring 716 is then sutured to the patient's body, thus restricting internal vascular disturbance during setup of the procedure and during use.

A hemostasis valve 718 is provided at the proximal section 714 of catheter guide 711 for receiving sheath 408 from cartridge 404. An irrigation port 719 is also located at the proximal section 714 to provide irrigation to the inner lumen 712 of the catheter guide 711. The proximal section 714 further includes an attachment area 720 configured to be attached to mounting clip 722, which provides a means for attachment of the catheter guide 711 to manipulator assembly 300. Mounting clip 722 can be permanently or releasably attached to the manipulator assembly 300.

FIG. 12 shows a cross-sectional view of catheter guide 711 along line A-A shown in FIG. 11b. As shown, vascular guide section 713 comprises an elongate tube 724 which extends the length of vascular guide section 713 and extends beyond the annular stop ring 716. Annular stop ring 716 is fixed to elongate tube 724 to provide a fixed length internal to a patient. Transition section 715 comprises a semi-ridged positioning jacket 726 along the length of transition section 715 between the suture ring 716 and the proximal section 714. Transition section 715 further comprises an elongate tube 728 extending from the hemostasis valve 718 through the positioning jacket 726 to a point proximal of the distal end of the transition section 715 and the suture ring 716. Located at the distal end of elongate tube 728, and contained within positioning jacket 726, is a joint septum 730 configured to receive the proximal end of elongate tube 724. In use, when the proximal end of elongate tube 724 is inserted into joint septum 730, a portion of elongate tube 724 is inserted into the distal end of elongate tube 728.

The positioning jacket 726 provides flexibility and support to the catheter guide 711 allowing for variances in the distance and alignment between the hemostasis valve 718 (i.e., the catheter introduction point) and the annular stop ring 716 (i.e., the patent access point). To facilitate its flexibility, positioning jacket 726 may be constructed of various known types of adjustable tubing, such as corrugated tubing, interlocking ball and socket segmented tubing, spiral wound metal tubing and skive cut solid tubing.

Figure 13A:
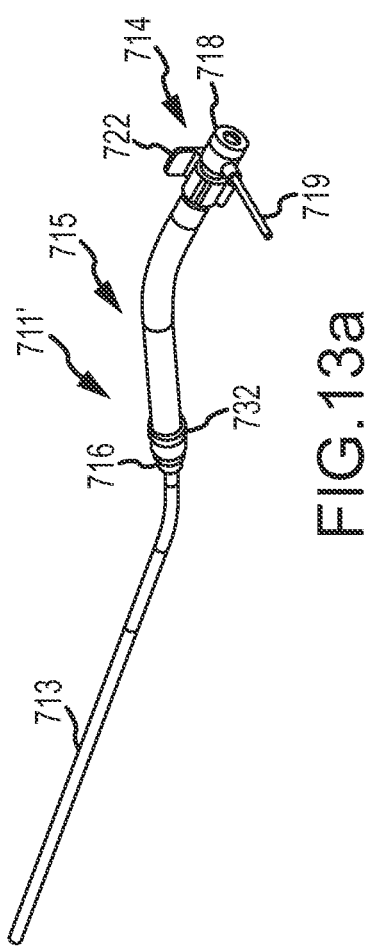
FIG. 13a is an isometric view of another embodiment of a medical device positioner.
Figure 13B:
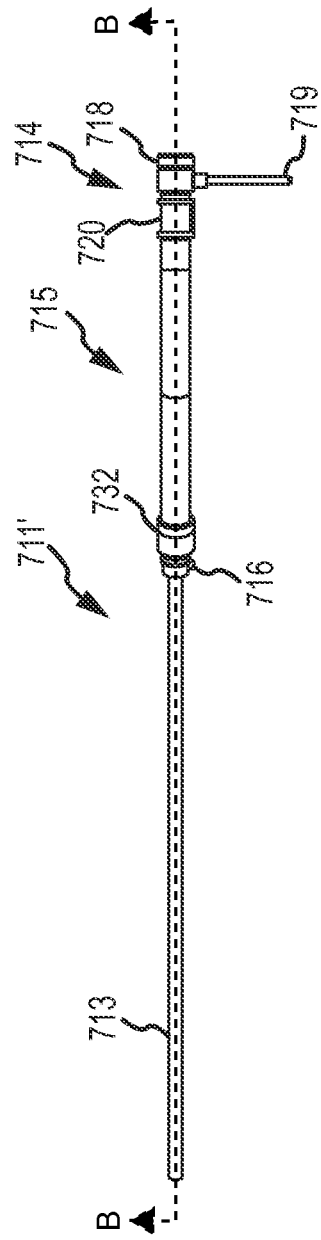

Another embodiment of a catheter guide 711' is illustrated in FIGS. 13a, 13b and 14, with most of the components being the same as in catheter guide 711. In catheter guide 711', a joint septum 732 is located at the proximal end of elongate tube 724' of vascular guide section 713. Elongate tube 724' thus does not extend into transition section 715. Rather, elongate tube 728' extends beyond the distal end of positioning jacket 726 and, in use, is inserted into joint septum 732. A portion of elongate tube 728' thus extends into elongate tube 724'. In this embodiment, it is evident that the elongate tube 724' of the vascular guide section 713 must have a larger inner diameter than the outer diameter of elongate tube 728', while in the embodiment of FIG. 12, the outer diameter of elongate tube 724 is smaller than the inner diameter of elongate tube 728.

Although numerous embodiments of this disclosure have been described above with a certain degree of particularity, those skilled in the art could make numerous alterations to the disclosed embodiments without departing from the spirit or scope of this disclosure. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present embodiments, and do not create limitations, particularly as to the position, orientation, or use of the embodiments. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device positioner for use with a remote catheter guidance system, the positioner comprising:
   a base configured to attach to the remote catheter guidance system;
   a first elongate support member attached at its proximal end to the base and including a receiving slot along its length that is sized and configured to receive at least a portion of an elongate medical device;
   a second elongate support member having a proximal end slideably engaged with the first elongate support member, the second support member further including a support guide located on a distal end, the support guide being sized and configured to receive at least a portion of the elongate medical device; and
   a locking member radially disposed around the first support member, the locking member being configured to rotatably move between a first position substantially covering the receiving slot and a second position exposing the receiving slot,
   wherein the proximal end of the second support member is configured to slideably move on the first support member between a first position and a second position in an axial direction relative to the first support member, and
   wherein the receiving slot and the support guide are configured to facilitate axial movement and substantially restrain lateral movement of the elongate medical device.

2. The medical device positioner of claim 1, wherein the first support member is substantially rigid.

3. The medical device positioner of claim 1, wherein the first support member is pivotably attached to the base.

4. The medical device positioner of claim 3, wherein the first support member is attached to the base with a ball and socket joint.

5. The medical device positioner of claim 3, wherein the base includes an orientation slot having a length and an orientation, the proximal end of the first elongate support member includes a pin adapted to fit into the orientation slot when the first elongate support member is attached to the base, the first elongate support member having a range of motion relative to the base, and, wherein the range of motion of the first elongate support member is determined by the length and the orientation of the orientation slot.

6. The medical device positioner of claim 1, wherein the elongate medical device is one of a catheter, a fixed sheath and a deflectable sheath.

7. The medical device positioner of claim 1, wherein the base comprises at least one mounting clip adapted to releasably mate with a mounting slot located on the remote catheter guidance system and to secure the base to the remote catheter guidance system when attached.

8. The medical device positioner of claim 1, wherein the base comprises a base support guide adapted to engage the elongate medical device and allow axial movement of the elongate medical device between the base and the first support member.

9. A medical device positioner for use with a remote catheter guidance system, the positioner comprising:
   a base configured to attach to the remote catheter guidance system;
   a first elongate support member attached at its proximal end to the base and including a receiving slot along its length that is sized and configured to receive at least a portion of an elongate medical device;
   a second elongate support member having a proximal end slideably engaged with the first elongate support member, the second support member further including a support guide located on a distal end, the support guide being sized and configured to receive at least a portion of the elongate medical device; and
   a locking member radially disposed around the first support member, the locking member being configured to rotatably move between a first position substantially covering the receiving slot and a second position exposing the receiving slot,
   wherein the proximal end of the second support member is configured to slideably move on the first support member between a first position and a second position in an axial direction relative to the first support member.

* * * * *